United States Patent [19]
Swerdloff et al.

[11] Patent Number: 4,518,413
[45] Date of Patent: May 21, 1985

[54] POLY-PHOSPHORODIAMIDE UREASE INHIBITORS AND UREASE INHIBITED UREA BASED FERTILIZER COMPOSITIONS

[75] Inventors: Michael D. Swerdloff, Parsippany; Jaroslav F. Kolc, Randolph; Milorad M. Rogic, Whippany, all of N.J.; Larry L. Hendrickson, Camillus, N.Y.

[73] Assignee: Allied Corporation, Morris Township, Morris County, N.J.

[21] Appl. No.: 501,673

[22] Filed: Jun. 6, 1983

[51] Int. Cl.³ ............................................. C05C 9/00
[52] U.S. Cl. ........................................ 71/28; 71/902
[58] Field of Search ............................. 71/11, 27–30, 71/902

[56] References Cited

U.S. PATENT DOCUMENTS 4,182,881  1/1980  Bayless et al. ..................... 546/22
4,222,948  9/1980  Alaimo et al. ............... 260/397.7 R
4,225,526  9/1980  Alaimo et al. ............... 260/397.7 R
4,242,325 12/1980  Bayless et al. ...................... 424/210

FOREIGN PATENT DOCUMENTS 830800  3/1960  United Kingdom .
1494774 12/1977  United Kingdom .

OTHER PUBLICATIONS

1978, CA, vol. 89, Abst. #89:89455k, Matzel et al.
1979, CA, vol. 90, Abst. #90:21340j, Oertel et al.
1979, CA, vol. 91, Abst. #91:122724p, Matzel et al.
1979, CA, vol. 91, Abst. #91:139619f, Heber et al.
1981, CA, vol. 94, Abst. #94:101951g, Vlek et al.
1981, CA, vol. 94, Abst. #94:139429f, Bayless et al.

Primary Examiner—Ferris H. Lander
Attorney, Agent, or Firm—Richard C. Stewart, II

[57] ABSTRACT

The invention relates to novel urease inhibited fertilizer compositions containing urea and a urease inhibiting amount of novel poly-phosphorodiamide compounds.

32 Claims, No Drawings

POLY-PHOSPHORODIAMIDE UREASE INHIBITORS AND UREASE INHIBITED UREA BASED FERTILIZER COMPOSITIONS

BACKGROUND OF THE INVENTION

1. Field of the Invention

This invention relates to novel poly-phosphorodiamide urease inhibitors and to urease inhibited urea based fertilizer compositions. More particularly, this invention relates to urease inhibited urea based fertilizer compositions which contain certain poly-phosphorodiamide compounds as the urease inhibitors, and methods of using such fertilizer compositions to increase plant yield. This invention also relates to compositions and methods of inhibiting the catalytic activity of soil urease by use such poly-phosphorodiamide compounds.

2 The Prior Art

It is well known in the art to use urea and urea compositions in fertilizers, for application to the soil. The effective life of such fertilizers, however, is of short duration wherever microbiological activity exists in the soil to which the fertilizer is applied. This is due to the fact that urea is hydrolyzed rapidly, and nitrogen is lost in the form of ammonia, when urea is placed under or on the surface of soil which contains urease.

Urease, a crystallizable enzyme occurring in numerous bacteria and fungi, as for example *Micrococcus urease,* catalyzes the conversion of urea into ammonia and carbon dioxide. The reactions are as follows:

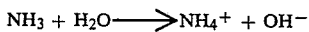

A portion of the ammonia thus formed is held by absorbing constituents of the soil and is available to plants as nutrient. However, a large amount of the ammonia may be lost to the air. A further problem resulting from the action of urease is that the accumulation of ammonium species in the soil may damage germinating seedlings and young plants.

One approach to reduction of problems resulting from the activity of soil urease toward soil applied urea is to find compounds that inhibit urease activity when applied to soils in conjunction with fertilizer urea. This approach has received considerable attention, and several classes of compounds have been used for this purpose.

For example, the prior art describes various phosphoro compounds which are useful as urease inhibitors. Illustrative of such prior art are East German Pat. Nos. 142,714; 212,026; 122,177; 122,621 and 130,936, and Great Britain Pat. No. 1,494,774, which patents describe various phosphorodiamidates as urease inhibitors. U.S. Pat. No. 4,242,325 describes a method of controlling the enzymatic decomposition of urea to ammonia and carbonic acid due to the action of urease, which method comprises exposing the enzyme to certain phosphoric triamide compounds. U.S. Pat. No. 4,182,881 describes the use of certain N-(diaminophosphinyl)arylcarboxyamide compounds as inhibitors of the enzyme urease in the urinary tract. U.S. Pat. No. 4,225,526 describes the use of 8-[(4-aminophenyl)-sulfonyl]amino-2-naphthalenyl phosphorodiamidate compounds as inhibitors of the enzyme urease, and U.S. Pat. No. 4,222,948 describes the use of ([(4-aminophenyl)sulfonylamino])phenyl phosphorodiamidate compounds as inhibitors of the enzyme urease.

Still other prior art describes phosphorictriamide compounds which are useful for other purposes, for example as flameproofing agents. For example, Great Britain Pat. No. 830,800 describes certain polyphosphoric triamide compounds which are useful as flame proofing agents.

SUMMARY OF THE INVENTION

In accordance with the present invention, there is provided a unique fertilizer composition comprising urea or a compound which is capable of forming urea in situ when subjected to the use conditions of the composition, and a "urease inhibiting effective amount" of one or more poly-phosphorodiamide compounds of the formula:

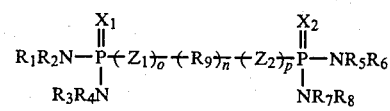

wherein:

o, n and p are the same or different, and are 0 and 1, with the proviso that at least one of o, n and p is 1;

$X_1$ and $X_2$ are the same or different, and are oxygen or sulfur;

$R_1$, $R_2$, $R_3$, $R_4$, $R_5$, $R_6$, $R_7$ and $R_8$ are the same or different and are hydrogen or alkyl having from 1 to about 4 carbon atoms;

$R_9$ is a substituted or unsubstituted divalent aminophosphinyl, alkylene, alkenylene, alkynylene, cycloalkylene, cycloalkenylene, or arylene group, which group may include one or more divalent oxygen, nitrogen, sulfonyl, sulfinyl, sulfur or carbamyl functions, wherein permissible substituents include one or more mercapto, hydroxy, amino, alkylamino, dialkylamino, arylamino, alkylmercapto, diaminophosphinyl, alkyl, alkoxy, sulfonic acid, halogen, O-diaminophosphinyl, S-diaminophosphinyl, N-diaminophosphinyl, N-(diaminophosphinyl)carbamyl, nitro or cyano groups; and $Z_1$ and $Z_2$ are the same or different and are individually divalent oxygen, sulfur, or a divalent amino or carbamyl moiety of the formula:

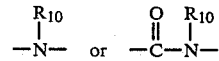

wherein $R_{10}$ is hydrogen, or substituted or unsubstituted cycloalkyl, alkyl, diaminophosphinyl or phenyl wherein permissible substituents are one or more halogen, nitro, N-diaminophosphinyl, O-diaminophosphinyl, S-diaminophosphinyl, N-(diaminophosphinyl)carbamyl, cyano, trifluoromethyl, alkylmercapto, alkoxy or mercapto groups, or any two $R_{10}$ substituents together may form an alkylene chain completing a 4, 5, 6, 7, or 8 membered ring structure.

In the present specification and claims, the term "poly-phosphorodiamide compounds" is used to refer to these compounds.

Another aspect of this invention relates to a method of enhancing the yield and/or growth of plants by distributing the fertilizer composition of this invention in the "plant growth media" in which plants are being grown within reach of the root system of the plants (hereinafter referred to as "root zone"). As herein, the term "plant growth media" refers to various natural and artificial media which support plant growth, including but not limited to soil, potting mixtures of organic and inorganic matter and artificial media such as polyurethane foam.

Yet another aspect of this invention relates to a method of inhibiting the urease catalyzed hydrolysis of urea at some situs, as for example a plant growth media, which comprises applying or distributing a "urease inhibiting effective amount" of one or more of the aforementioned poly-phosphorodiamide compounds to the plant growth media or other situs prior to, after or in conjunction with the application of urea to said plant growth media or other situs, and to a composition for carrying out such method. As used herein, a "urease inhibiting effective amount" is an amount of such polyphosphorodiamide compounds which when admixed with urea, is capable of inhibiting the urease catalyzed hydrolysis of such urea to any extent.

It has been discovered that by distributing an urease inhibiting effective amount of one or more of the poly-phosphorodiamide compounds in the plant growth media, the activity of urease in the media is suppressed thereby preventing rapid loss of urea from the media. Furthermore, by proper distribution of the poly-phosphorodiamide compounds in the plant growth media, the inhibition of the action of urease is effective over a prolonged period of time.

DETAILED DESCRIPTION OF THE INVENTION

The application of a urease inhibiting effective amount of one or more of the above-identified poly-phosphorodiamide compounds to a composition, or at some situs as for example a plant growth media is essential for the practice of this invention. While these compositions can be effectively used to inhibit urease at many different situs, they are preferred for use in a plant growth media. When these compositions are used in the preferred embodiments, the plant growth media is preferably impregnated with at least about 0.02 parts of said one or more poly-phosphorodiamide compounds per 1,000,000 parts of the plant growth media. Hereinafter, the abbreviation of "p.p.m" designates parts of one or more poly-phosphorodiamide compounds per million parts of soil or other plant growth media. In the preferred embodiments of this invention, the amount of said one or more poly-phosphorodiamide compounds impregnated in the plant growth media is from about 0.02 to about 5000 p.p.m, and in the particularly preferred embodiments of the invention is from about 0.1 to about 1000 p.p.m. on the same basis. Amongst these particularly preferred embodiments, most preferred are those embodiments in which the weight percent of said one or more poly-phosphorodiamidate compounds is from about 1 to about 500 p.p.m.

Within the aforementioned limitations, the preferred amounts of the one or more poly-phosphorodiamide compounds impregnated or distributed in the growth media are dependent upon the particular situation. Thus, in determining the amount to be employed, consideration is made not only of the treatment need, i.e., soil pH, temperature, soil type, etc., but also of the mode of application to soil. When the one or more polyphosphorodiamide compounds are applied in a broadcast application, the amount in p.p.m. is frequently less than in row or band application where, for a substantial depth and width within the vicinity of application, there can be a very high concentration of the one or more poly-phosphorodiamide compounds. When application is made near the root zone or growing plants or when application is made immediately prior to seeding or transplanting, the amounts supplied are frequently at a lower rate than when application is made at the end of the growing season to prepare the soil for the following season. By dispersing very large dosages in the plant growth media, a prolonged inhibition of urease activity can be obtained over a period of many months. The concentration of the one or more polyphosphorodiamide compounds is eventually reduced to a minimum by decomposition in the soil.

In one method for carrying out the present invention, one or more polyphosphorodiamide compounds are distributed throughout the plant growth media in a broadcast application, such as by spraying, dusting, distributing in irrigation water, etc. In such application, the one or more phosphorodiamide compounds are supplied in amounts sufficient to permeate the growing area of the plant growth media with a urease inhibiting effective amount of such compounds. In field administration, the one or more polyphosphorodiamide compound can be distributed in the plant growth media in an the amount and through such cross-section of the plant growth media as to provide for the presence therein of an effective amount of such compounds. It is usually preferred that the urease inhibiting one or more polyphosphorodiamide compounds be distributed below the surface of the media.

In another method for carrying out the present invention, one or more poly-phosphorodiamide compounds are administered to a plant growth media in a band or row application. In such application, administration is made with or without a carrier in amounts sufficient to supply to the soil or growth media a concentration of the one or more poly-phosphorodiamide compound which can be as high as 5000 p.p.m. or more. After administration with or without discing or dragging, subsequent irrigation or rainfall distributes the one or more poly-phosphorodiamide compounds throughout the plant growth media.

In one embodiment of the present invention, the one or more poly-phosphorodiamide compounds are distributed throughout the plant growth media prior to seeding or transplanting the desired crop plant.

In another embodiment, the soil in the root zone of growing plants is treated with the one or more poly-phosphorodiamide compounds in an amount sufficient to inhibit the action of urease, but sublethal to plant growth. By following such practice, no adverse effect is exerted by the one or more poly-phosphorodiamide compounds upon growth of seeds or plants. Oftentimes, it is desirable to treat the soil or plant growth media adjacent to plants, and this procedure may be carried out conveniently in side-dressing operations.

In a further embodiment, soil or plant growth media can be treated with the one or more poly-phosphorodiamide compounds following harvest to prevent rapid loss of urea, and to prevent the build-up of soil urease. Such practice conserves the soil nitrogen for the following growing season. In such application, the upper limit is primarily an economic consideration.

In an additional embodiment, the soil or plant growth media is treated with the one or more poly-phosphorodiamide compounds in conjunction with the application of urea or one or more urea precursor compounds capable of forming urea in situ on application to the plant growth media. Urea is a well known, commercially available compound and will not be discussed herein in detail. Illustrative of compounds which are believed to form urea on addition to the soil and are water soluble and formaldehyde condensation products, as for example methylolureas, methyleneureas and mixtures thereof. These products and a method for their preparation is described in detail in U.S. Pat. No. 3,462,256. Still other useful sources of urea are water-insoluble urea formaldehyde condensation products such as ureaform. Illustrative of useful water-insoluble urea and formaldehyde condensation products are those whose preparation and use are described in detail in U.S. Pat. Nos. 3,677,736 and 4,033,745.

The composition of this invention which includes urea and optionally other micro- or macro-nutrients can be conveniently used in the practice of the method of this invention to increase yields in a wide variety of plants including legume crop plants and cereal crop plants. For example, the required amounts of the fertilizer composition of this invention can be applied to the soil within the root zone of the plant to obtain the desired increase in plant yield. The rate of application will depend on a number of factors, such as environmental conditions, type of crop plant and the like. The composition is usually applied at a rate of from about 5 to about 600 lbs. of urea nutrient per acre in a total applied aqueous volume of from about 3 to about 1500 gallons per acre. In the preferred embodiments of the method of this invention, the composition is applied at a rate of from about 2 to about 100 pounds of urea per acre in a total applied aqueous volume of from about 6 to about 250 gallons per acre, and in the particularly preferred embodiments at a rate of from about 3 to about 30 pounds per acre in a total volume of from about 9 to about 25 gallons per acre. The composition can be used in the soil or applied to the foliage of the plant, upon the media, or the roots of plants without injuring either the foliage, seeds or roots at any time during the growing cycle. Because of the action of the novel urease inhibitors present in the composition, all or a portion of the urease present at the situs of application will be inhibited and greater amounts of urea nutrients will be made available to the plant for longer periods of time.

The urease inhibiting method of the present invention can be carried out by distributing the one or more poly-phosphorodiamide compounds in an unmodified form through a plant growth media. The present invention also embraces distributing one or more such compounds as a constituent in liquid or finely divided solid to form urease inhibition compositions. The concentration of one the or more poly-phosphorodiamide compounds in the urease inhibition compositions of this invention to be employed for the treatment of growth media is not critical and can vary considerably provided a urease inhibition effective amount of the one or more polyphosphoroamide compounds is supplied to the growth media. In general, good results are obtained with liquid compositions containing at least about 0.00001 percent by weight of one or more poly-phosphorodiamide compounds based on the total weight of the composition. In the preferred embodiments of this invention, the weight percent of the one or more poly-phosphorodiamide compounds is from about 0.0001 to about 98 and in the particularly preferred embodiments of the invention the weight percent of the one or more polyphosphorodiamide compounds is from about 0.01 to about 50 weight percent. Amongst these particular preferred embodiments of this invention, most preferred are those embodiments of the invention in which the weight percent of said one or more poly-phosphorodiamide compounds is from about 0.10 to about 20 weight percent. Liquid or dust compositions in which the one or more poly-phosphorodiamide compounds are present in higher concentration can be utilized as such or can be employed as concentrate compositions to be diluted to prepare actual treating compositions.

In the urease inhibiting composition of this invention, the one or more poly-phosphorodiamide compounds can be modified with one or more additaments or soil treating adjuvants including water, petroleum distillates or other liquid carriers, surface-active dispersing agents, inert finely divided solids, urea or urea precursor compounds, and reduced nitrogen fertilizers, and other plant micro- or macronutrients. These adjuvants cooperate with the one or more poly-phosphorodiamide compounds so as to facilitate the practice of the method of the present invention and to obtain an improved result. Preferred adjuvants are surface-active dispersing agents, inert finely divided solids, and especially urea fertilizers. The amount of urea or urea precursor compound included in the composition of this invention is not critical to the unique advantages thereof, and any amount of urea or such compound used inconventional fertilizers can be in the conduct of this invention. Normally, the amount employed will vary widely depending on a number of factors, including the times and frequency of application. In the preferred embodiments of the invention, the quantity of urea or urea precursor compound may vary from about 0.5 to about 95 weight percent based on the total weight of the composition and in the particularly preferred embodiments may vary from about 1 to about 50 weight percent on the same basis. In the most preferred embodiments of this invention, the quantity of urea or urea presursor compound will vary from about 3 to about 40 weight percent on the aforementioned basis. The composition of this invention may include other micronutrients and/or macronutrients known to those of skill in the art for inclusion in fertilizer compositions. For example, the composition may include sources of potassium, sulfur, phosphorus, boron, zinc, iron, manganese, copper, molybdenum, cobalt and like micronutrients and macronutrients which may be deficient in the soil. The composition may also include plant growth regulators, as for example auxins, cytokinins and the like, as well as pesticides such as insecticides, miticides, herbicides, nematocides and the like. Depending upon the concentration of the one or more poly-phosphorodiamide compounds, augmented compositions can be distributed in the soil or plant growth media without further modification or can be considered as concentrates and subsequently diluted with additional inert carrier to produce the ultimate treating composition.

Liquid urease inhibiting compositions containing the desired amount of the one or more poly-phosphorodiamide compounds can be prepared by dispersing the latter in one or more liquid carriers such as water or an organic solvent with or without the aid of a suitable surface active dispersing agent or emulsifying agent. Suitable organic solvents include acetone, diisobutylketone, methanol, ethanol, isopropyl alcohol, diethyl ether, toluene, methylene chloride, chlorobenzene and petroleum distillates. The preferred organic solvents are those which are of such volatility that they leave little permanent residue in the growth media. Dispersing and emulsifying agents which can be employed in liquid compositions include condensation products of alkylene oxides with phenols and organic acids, alkylaryl sulfonates, polyoxyalkylene derivatives or sorbitol ester, sugar esters, complex ether alcohols, mahogany soaps and the like. The surface active agents are generally employed in the amount of from about 1 to about 20 percent by weight of the one or more poly-phosphorodiamide compounds.

Solid urease inhibiting compositions containing the active one or more poly-phosphorodiamide compounds can be prepared by dispersing the latter in finely divided inert solid carriers such as talc, chalk, gypsum, vermiculite, bentonite and the like, fuller's earth, attapulgite and other clays, various solid detergent dispersing agents and solid fertilizer compositions. In preparing such compositions, the carrier is mechanically ground with one or more solid poly-phosphorodiamide compounds; wet with one or more liquid polyphosphorodiamide compounds; or wet with a solution or dispersion of one or more solid or liquid poly-phosphorodiamide compounds in a volatile organic solvent. Depending upon the proportions of ingredients, these solid urease inhibiting compositions can be employed without further modification or be considered concentrates and subsequently further diluted with solid surface active dispersing agents, talc, chalk, gypsum or the like to obtain the desired treating composition. Furthermore, such concentrate compositions can be dispersed in water with or without added dispersing agent or agents to prepare aqueous soil treating compositions.

The required amount of the one or more polyphosphorodiamide compounds contemplated herein may be applied per acre treated in from about 1 to about 200 gallons or more of liquid carrier and/or diluent or in from about 5 to about 500 pounds of inert solid carrier and/or diluent. The concentration in the liquid concentrate will usually vary from about 10 to about 95 percent by weight and in the solid formulations from about 0.5 to about 90 percent be weight. Satisfactory sprays, dusts, or granules for general use contain from about ½ to about 15 pound of active one or more polyphosphorodiamide compounds per acre.

The compounds contemplated herein prevent or retard the urease catalyze hydrolysis of urea, and they have relatively high residual activity. With respect to plants they have a high margin of safety in that when used in sufficient amount to inhibit the activity of urease, they do not burn or injure the plant, and they resist weathering which includes wash-off caused by rain, decomposition by ultra-violet light, oxidation, or hydrolysis in the presence of moisture or, at least such decomposition, oxidation, and hydrolysis as would materially decrease the desirable urease inhibiting characteristic of the compounds or impart undesirable characteristics, for instance, phytotoxicity, to the compounds. The compounds are so chemically inert that they are compatible with substantially any other constituents of the spray schedule, and they may be used in the soil, upon the seeds, or the roots of plants without injuring either the seeds or roots of plants.

While the composition and method of this invention are particularly suited for agricultural applications for prevention or inhibition of urease catalyzed hydrolysis of urea, they can also be used in other applications where inhibition of the activity of urease is desired. For example, such other applications include use in animal litters, as feed additives, pharmaceutical applications, diaper treatments, urease inhibition in mammalian urinary tracts, and the like. It should be noted that while all of the above-described poly-phosphorodiamide compounds exhibit some level of urease inhibiting activity, the particularly active compound employed in one application may not necessarily be useful in another application. Thus, in the selection of a particular active material or the amounts thereof for use in an application, such factors as toxicity of the material, the environment in which the material will be used, level of urease inhibition desired and the like must be considered in selecting such material.

The poly-phosphorodiamide compounds which are employed as urease inhibitors in the composition and method of this invention are those of the formula:

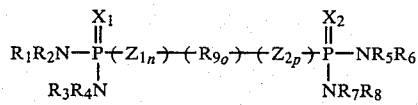

wherein:

o, n and p are the same or different and are 1 or 0, with the proviso that at least one of o, p and n is 1

$X_1$ and $X_2$ are the same or different and are oxygen or sulfur;

$R_1$, $R_2$, $R_3$, $R_4$, $R_5$, $R_6$, $R_7$ and $R_8$ are the same or different and are hydrogen or alkyl having from 1 to about 4 carbon atoms;

$R_9$ is a substituted or unsubstituted divalent aminophosphinyl, alkylene, alkenylene, alkynylene, cycloalkylene, cycloalkenylene, or divalent aromatic group which group may include one or more divalent oxyen, nitrogen, sulfonyl, sulfinyl, sulfur or carbamyl functions, wherein permissible substituents include one or more alkylmercapto, diaminophosphinyl, hydroxy, amino, alkylamino, dialkylamino, arylamino, alkyl, alkoxy, sulfonic acid, halogen, S-diaminophosphinyl O-diaminophosphinyl, N-diaminophosphenyl, N-(diaminophosphinyl)carbamyl, nitro or cyano groups; and $Z_1$ and $Z_2$ are the same or different and are divalent oxygen, sulfur, or a divalent amino or carbamyl moiety of the formula:

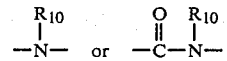

wherein: $R_{10}$ is hydrogen or substituted or unsubstituted cycloalkyl, alkyl, diaminophosphinyl, or phenyl wherein permissible substituents include one or more halogen, nitro, N-diaminophosphinyl O-diaminophosphinyl, S-diaminophosphinyl, N-(diaminophosphinyl)-carbamyl, cyano, trifluoromethyl, alkylmercapto, alkoxy and mercapto groups, or any two $R_{10}$ substituents together may form an alkylene chain completing a 4, 5, 6, 7, or 8 membered ring structure.

Illustrative of permissible $R_1$, $R_2$, $R_3$, $R_4$, $R_5$, $R_6$, $R_7$ and $R_8$ substituents are hydrogen, methyl, ethyl, isopropyl, propyl, butyl and the like.

Exemplary of permissible $R_9$ groups are methylene, ethylene, propylene, isopropylene, butylene, pentylene, hexylene, 2,3-dichloropropylene, dichloromethylene, 1,4-dioxo-2,3-dichlorobutylene, 1,3-dioxo-2,2-difluoropropylene, phenylene, 4-methylenebenzylene, triethylenedioxide, diethyleneoxide, cyanomethylene, 1,3-dioxo-2-chloro-propylene, 2-carbamylphenylene, biphenylene, naphthylene, anthrylene, xylylene, (1-methylethylidene)diphenylene, menthanylene, cyclohexylene, ethylenemercaptoethylene, 3-nitrocyclo-1,4-cyclohexenyl, butylene-(N-diaminophosphinyl)aminopropylene, 2-methylmercapto-1,4-phenylene, 2-methyl-1,4-phenylene, aminophosphinyl, and the like.

Illustrative $Z_1$ and $Z_2$ groups include divalent oxygen, sulfur, amino, methylamino, propylamino, ethylamino, phenylamino, N-(4-nitrophenyl)amino, N-(4-trifluoromethylphenyl)amino, trichloromethylamino, 2,2-dichloroethylamino, 3-methylmercaptophenylamino, carbamyl, N-methylcarbamyl, N-phenylcarbamyl, N-(2,4-dimethylphenyl)carbamyl, N-(diaminophosphinyl)amino, N-(diaminophosphenyl)carbamyl, N,N'-piperazine, methoxymethylamino, N(N',N'-dimethylphosphinyl)amino, N-methylcarbamyl, N-(dichloromethyl)carbamyl, N-(2-nitroethyl)carbamyl, and the like.

Illustrative $R_{10}$ groups include hydrogen, methyl, ethyl, isopropyl, cyclohexyl, cyclobutyl, phenyl, diaminophosphinyl, 2-chloroethyl, 3-bromopropyl, 4-nitorphenyl, 3-trifluoromethyl, 4-methylmercaptobutyl, 3-cyanohexyl, 2-methoxyethyl, 4-(O-diaminophosphinyl)-phenyl, 3-(N-diaminophosphinyl)carbamylphenyl, 4-(N-diaminophosphinyl)phenyl, 2-(S-diaminophosphinyl)phenyl, 2-(N-diaminophosphinyl)ethyl, 6-(O-diaminophosphyl)-hexyl, 3-bromocyclohexyl, and the like.

The following compounds are illustrative of polyphosphorodiamide compounds within the purview of the above structural formula which can be prepared simply by selecting appropriate reactants for use in the procedures described below and which can be employed in the practice of this invention.

1,4-Benzenedimethanol-bis-phosphorodiamidate
1,3-Benzenedimethanol-bis-phosphorodiamidate
2,6-Pyridinedimethanol-bis-phosphorodiamidate
Phosphorodiamidic acid (1-methylethylidene)di-4,1-cyclohexylene ester
Phosphorodiamidic acid 2-methyl-1,4-phenylene ester
Phosphorodiamidic acid 2,6-dichloro-1,4-phenylene ester
Phosphorodiamidic acid 2,6-dimethyl-1,4-phenylene ester
Phosphorodiamidic acid 2-nitro-1,4-phenylene ester
Phosphorodiamidic acid 2-tert-butyl-1,4-phenylene ester
Phosphorodiamidic acid 2,3,5,6-tetrachloro-1,4-phenylene ester
Phosphorodiamidic acid 2-isopropyl-1,4-phenylene ester
Phosphorodiamidic acid 1,4-phenylene-2-(sulfonic acid)ester
Phosphorodiamidic acid 2-methyl-1,3-phenylene ester
Phosphorodiamidic acid 4,6-dichloro-1,3-phenylene ester
Phosphorodiamidic acid 4-bromo-1,3-phenylene ester
Phosphorodiamidic acid 2-nitro-1,3-phenylene ester
N,N'-Bis-(diaminophosphinyl)oxamide
N,N'-Bis-(diaminophosphinyl)urea
N,N'-Bis-(diaminophosphinyl)malonamide
N,N'-Bis-(diaminophosphinyl)-2-methylmalonamide
N,N'-Bis-(diaminophosphinyl)-2-bromomalonamide
N,N'-Bis-(diaminophosphinyl)-2,2-dichloromalonamide
N,N'-Bis-(diaminophosphinyl)-meso-2,3-dichlorosuccinamide
N,N'-Bis-(diaminophosphinyl)-threo-2,3-dibromosuccinamide
N,N'-Bis-(diaminophosphinyl)-3,4-dichloroadipamide
N,N'-Bis-(diaminophosphinyl)-3-tert-butyladipamide
N,N'-Bis-(diaminophosphinyl)-2,2,4,4-tetrachloroglutamamide
N,N'-Bis-(diaminophosphinyl)-2-(4'-nitrophenyl)-malonamide
N,N'-Bis-(diaminophosphinyl)-1,4-benzenedicarboxamide
N,N'-Bis-(diaminophosphinyl)-1,3-benzenedicarboxamide
N,N',N''-Tris-(diaminophosphinyl)-1,3,5-benzenetricarboxamide
N,N'-Bis-(diaminophosphinyl)-2,6-naphthalenedicarboxamide
N,N'-Bis-(diaminophosphinyl)-1,4-naphthalenedicarboxamide
N,N'-Bis-(diaminophosphinyl)-1,6-naphthalenedicarboxamide
N,N'-Bis-(diaminophosphinyl)-2,5-pyridinedicarboxamide
N,N'-Bis-(diaminophosphinyl)-2,6-pyridinedicarboxamide
N,N'-Bis-(diaminophosphinyl)-2,5-furandicarboxamide
N,N'-Bis-(diaminophosphinyl)-2,5-thiophenedicarboxamide
N,N'-Bis-(diaminophosphinyl)-2,5-quinolinedicarboxamide
2,6-Pyridinedimethanol-bis-thiophosphorodiamidate
Phosphorodiamidic acid 2,4-pyridinylene ester
Phosphorodiamidic acid 2,6-pyridinylene ester
Phosphorodiamidic acid 4,6-pyrimidinylene ester
Phosphorodiamidic acid 4,7-(1,10-phenanthrolinylene)ester
Phosphorodiamidic acid 2,4-quinolinylene ester
Phosphorodiamidic acid 2,5-(1,4-benzoquinonylene)ester
Phosphorodiamidic acid 5,8-(1,4-naphthoquinonylene)ester
Phosphorodiamidic acid 2,4-(5-nitropyrimidinylene)ester
Phosphorodiamidic acid 1,8-anthraquinonylene ester
Phosphorodiamidic acid 2',5'-acetophenonylene ester
Phosphorodiamidic acid 2,4-benzophenonylene ester
Phosphorodiamidic acid 4,4'-benzophenonylene ester
Phosphorodiamidic acid 2,4,6-pyrimidinylene ester
N,N',N''-Tris-(diaminophosphinyl)-2,4,6-triaminopyrimidine
N,N-Bis-(diaminophosphinyl)-2,4-dimercaptopyrimidine
N,O-Bis-(diaminophosphinyl)-4-aminophenol
N,O-Bis-(diaminophosphinyl)-3-aminophenol
N,S-Bis-(diaminophosphinyl)-4-aminothiophenol
N,S-Bis-(diaminophosphinyl)-3-aminothiophenol
N,S-Bis-(diaminophosphinyl)-5-amino-1,3,4-thiadiazole-2-thiol
N,S-Bis-(diaminophosphinyl)-2-amino-6-purinethiol
N,O-Bis-(diaminophosphinyl)-2-amino-6-hydroxypyridine
N,O-Bis-(diaminophosphinyl)-2-amino-4-hydroxy-6-methylpyrimidine
N,O,S-Tris-(diaminophosphinyl)-4-amino-6-hydroxy-2-mercaptopyrimidine
N,O-Bis-(diaminophosphinyl)-1-amino-4-hydroxyanthraquinone
N,S-Bis-(diaminophosphinyl)-4-amino-2-mercaptopyrimidine N,S-Bis-(diaminophosphinyl)-3-amino-5-mercapto-1,2,4-triazole
O,S-Bis-(diaminophosphinyl)-4-hydroxy-2-mercapto-6-methylpyrimidine
O,S-Bis-(diaminophosphinyl)-4-hydroxy-2-mercapto-6-methylpyrimidine
O,S-Bis-(diaminophosphinyl)-6-hydroxy-8-mercaptopurine
O,S-Bis-(diaminophosphinyl)-4-hydroxy-2-mercaptopyrimidine
O,O,S-Tris-(diaminophosphinyl)-2-mercapto-6,8-purinediol
N,N'-Bis-(diaminophosphinyl)-4-diaminobutane
N,N'-Bis-(diaminophosphinyl)-1,5,-diaminopentane
N,N'-Bis-(diaminophosphinyl)-1,8-diaminooctane
N,N'-Bis-(diaminophosphinyl)-1,4-diamino-2-butanone
N,N'-Bis-(diaminophosphinyl)-4,4'-diaminophenylamine
N,N'-Bis-(diaminophosphinyl)-3,3'-iminobispropylamine
N,N'-Bis-(diaminophosphinyl)-1,2-diamino-2-methylpropane
Phosphorodiamidic acid 4,6-(2-methylmercapto pyrimidinylene ester
Phosphorodiamidic acid 1,4-naphthylene ester
Phosphorodiamidic acid 2,7-naphthylene ester
Phosphorodiamidic acid 3,6-pyridazylene ester
Phosphorodiamidic acid 1,5-(1,2,3,4-tetrahydronaphthylene ester
N,N'-Bis-(diaminophosphinyl)-1,4-phenylenediamine
N,N'-Bis-(diaminophosphinyl)-1,3-phenylenediamine
N,N'-Bis-(diaminophosphinyl)-2-nitro-1,4-phenylenediamine
N,N'-Bis-(diaminophosphinyl)benzidine
N,N'-Bis-(diaminophosphinyl)-1,4-diaminoanthraquinone
N,N'-Bis-(diaminophosphinyl)-2,6-diaminoanthraquinone
N,N'-Bis-(diaminophosphinyl)-1,5-diaminonaphthalene
N,N'-Bis-(diaminophosphinyl)-3,6-diaminoacridine
N,N'-Bis-(diaminophosphinyl)-4-aminophenylsulfone
N,N'-Bis-(diaminophosphinyl)-2,6-diaminoanthraquinone
N,N'-Bis-(diaminophosphinyl)-3,5-diamino-2,6-dimethoxypyridine
N,N'-Bis-(diaminophosphinyl)-2-aminophenylsulfide
N,N'-Bis-(diaminophosphinyl)-2,2'-ethylenedianiline
N,N'-Bis-(diaminophosphinyl)-4,4'-methylenedianiline
N,N'-Bis-(diaminophosphinyl)diaminomaleonitrile
N,N'-Bis-(diaminophosphinyl)-2,4-diamino-5-phenylthiazole
N,N'-Bis-(diaminophosphinyl)-2,5-diaminopyridine
N,N'-Bis-(diaminophosphinyl)-2,6-diaminopyridine
N,N'-Bis-(diaminophosphinyl)-4,6-diaminopyrimidine
N,N'-Bis-(diaminophosphinyl)-4,4'-diaminostilbene
N,N'-Bis-(diaminophosphinyl)-2,4-diaminotoluene
N,N'-Bis-(diaminophosphinyl)-2,6-diaminotoluene
N,N'-Bis-(diaminophosphinyl)-3,5-diamino-1,2,4-triazole
N,N'-Bis-(diaminophosphinyl)-5,8-diaminoquinoline
N,N'-Bis-(diaminophosphinyl)-1,3-benzenedithiol
Phosphorodiamidic acid 1,3,5-phenylene ester
Phosphorodiamidic acid 2,4,4'-benzophenonylene ester
N,N'-Bis-(diaminophosphinyl)-4-chloro-2,6-diaminopyrimidine
N,N'-Bis-(diaminophosphinyl)-2-chloro-4,6-diamino-1,3,5-triazine
N,N'-Bis-(diaminophosphinyl)-1,4-diamino-2-butene
N,N'-Bis-(diaminophosphinyl)-1,6-diamino-3-hexene
Phosphorodiamidic acid 1,3-propylene ester
Phosphorodiamidic acid 1,4-butylene ester
Phosphorodiamidic acid 2,5-hexylene ester
Phosphorodiamidic acid 1,4-cyclohexylene ester
Phosphorodiamidic acid 2,5-dimethyl-2,5-hexylene ester
O,O-Bis-(diaminophosphinyl)-2,5-dihydroxy-1,4-dithiane
O,O,S-Tris-(diaminophosphinyl)-4,6-dihydroxy-2-mercaptopyrimidine
O,O-Bis-(diaminophosphinyl)-diethanolamine
O,O-Bis-(diaminophosphinyl)-2-hydroxyethyl ether
O,O-Bis-(diaminophosphinyl)-2-hydroxyethyl disulfide
O,O-Bis-(diaminophosphinyl)-2-hydroxyethyl sulfide
O,O-Bis-(diaminophosphinyl)-2-hydroxyethyl sulfone
O,O-Bis-(diaminophosphinyl)-4-hydroxybenzyl alcohol
O,O-Bis-(diaminophosphinyl)-4-hydroxyphenethyl alcohol
N,O-Bis-(diaminophosphinyl)-3-aminobenzyl alcohol
N,O-Bis-(diaminophosphinyl)-2-aminophenethyl alcohol
N,N'-Bis-(diaminophosphinyl)-4-aminophenethylamine
N,N',N''-Tris-(diaminophosphinyl)spermidine
N,N',N'',N'''Tetrakis-(diaminophosphinyl)spermine
S,S-Bis-(diaminophosphinyl)-1,9-dimercaptononane
S,S-Bis-(diaminophosphinyl)-2,5-dimercapta-1,3,4-thiadiazole
S,S-Bis-(diaminophosphinyl)-1,8-dimercaptooctane
O,O-Bis-(diaminophosphinyl)-3,6-dithia-1,8-octanediol
S,S-Bis-(diaminophosphinyl)-4,4'-dimercaptophenyl ether
S,S-Bis-(diaminophosphinyl)-α,α'-dimercapto-p-xylene
O,S-Bis-(diaminophosphinyl)-4-mercaptophenol
O,S-Bis-(diaminophosphinyl)-6-mercapto-1-hexanol
N,S-Bis-(diaminophosphinyl)-6-amino-2-mercaptobenzothiazole
N,O-Bis-(diaminophosphinyl)-4-amino-N-(hydroxymethyl)phthalimide
N,O-Bis-(diaminophosphinyl)-4'-amino-3-hydroxystilbene
O,O-Bis-(diaminophosphinyl)-1,3-dihydroxy-2-propanone
Imidodiphosphoramide
Pyrophosphoramide
Diimidotriphosphoramide
Phosphorodiamidic acid 1,4-but-2-ynylene ester
O,N-Bis-(diaminophosphinyl)-4-hydroxybenzamide
N-(diaminophosphinyl)-3-(N-diaminophosphinylamino)benzamide
O,N-Bis-(diaminophosphinyl)-2-(4'-hydroxyphenyl)ethylamine
N,N'-Bis-(diaminophosphinyl)glycinamide
O,O-Bis-(diaminophosphinyl)-4-hydroxyphenylacetamide
N,O-Bis-(diaminophosphinyl)-4-aminophenylacetamide
N,N-Bis-(diaminophosphinyl)-DL-3-amino-3-phenylpropionamide
N,N'-Bis-(diaminophosphinyl)-6-aminohexanamide
N,O-Bis-(diaminophosphinyl)-DL-3-hydroxybutyramide
N,S-Bis-(diaminophosphinyl)-2-mercaptoacetamide
N,S-Bis-(diaminophosphinyl)-3-mercaptopropionamide
N,N'-Bis-(diaminothiophosphinyl)oxamide
N,N'-Bis-(diaminothiophosphinyl)-2,2-dibromomalonamide
N,N'-Bis-(diaminothiophosphinyl)-meso-2,3-dichlorosuccinamide Thiophosphorodiamidic acid 1,4-phenylene ester
1,4-Benzenedimethanol-bis-thiophosphorodiamidate
N,N'-Bis-(diaminothiophosphinyl)-1,4-benzenecarboxamide
Thiophosphorodiamidic acid 2,6-pyridinylene ester
N,N'-Bis-(diaminothiophosphinyl)-1,6-diaminohexane
N,O-Bis-(diaminothiophosphinyl)-4-aminophenol
N,S-Bis-(diaminothiophosphinyl)-3-aminothiophenol
N,N'-Bis-(diaminothiophosphinyl)piperazine
N,N'-Bis-(diaminothiophosphinyl)-1,4-diaminoanthraquinone
Thiophosphorodiamidic acid 1,3,5-phenylene ester
Imidodithiophosphoramide
Pyrodithiophosphoroamide
Diimidotrithiophosphoramide
S,S-Bis-(diaminothiophosphinyl)-1,6-dimercaptohexane
O,O,S-Tris-(diaminothiophosphinyl)-4,6-dihydroxy-2-mercaptopyrimidine
S,S-Bis-(diaminothiophosphinyl)-2,5-dimercapto-1,3,4-thiadiazole
O,N-Bis-(diaminothiophosphinyl)-3-hydroxybenzamide
O,O-Bis-(diaminothiophosphinyl)-1,3-dihydroxy-2-propanone
O,O-Bis-(diaminothiophosphinyl)-2-hydroxyethyl ether
O,S-Bis-(diaminothiophosphinyl)-4-hydroxy-2-mercapto-6-propylpyrimidine
O,S-Bis-(diaminothiophosphinyl)-4-mercaptophenol Preferred for use in the practice of this invention are polyphosphorodiamide compounds in which:

X is oxygen;

$R_1, R_2, R_3, R_4, R_5, R_6, R_7$ and $R_8$ are hydrogen;

$R_9$ is aminophosphinyl, alkylene, phenylene, alkylenephenylalkylene, alkylenephenylene, alkyleneaminoalkylene, or dioxoalkylene, either substituted or unsubstituted with one or more halogen, alkyl, nitro, cyano, N-diaminophosphinyl, O-diaminophosphinyl, N-(diaminophosphinyl)carbamyl, S-diaminophosphinyl, trihalomethyl or alkoxy substituents;

$Z_1$ and $Z_2$ are the same or different and are individually divalent oxygen, or a moiety of the formula:

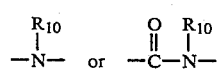

wherein:

$R_{10}$ is hydrogen, diaminophosphinyl, cycloalkyl, alkyl, alkyl substituted with one or more halogen groups, phenyl or phenyl substituted with one or more alkyl, nitro, aryloxy, halogen, or trihalomethyl, or two $R_{10}$ substituents together form an alkylene chain completing a 4, 5, or 6 membered ring structure which may be substituted with one or more of the aforementioned substituents.

Particularly preferred for use in this invention are polyphosphorodiamide compounds in which:

X is oxygen;

$R_1, R_2, R_3, R_4, R_5, R_6, R_7$ and $R_8$ are hydrogen;

$R_9$ is alkylene having from 1 to about 6 carbon atoms, alkyleneaminoalkylene having from about 2 to about 8 carbon atoms, or alkylphenylene having from about 7 to about 14 carbon atoms; and $Z_1$ and $Z_2$ are the same or different and are divalent oxygen, or a moiety of the formula:

wherein: $R_{10}$ is hydrogen, diaminophosphinyl, cyclohexyl, or substituted or unsubstituted alkyl or phenyl wherein permissible substituents are one or more halo substituents or any two $R_{10}$ groups together may form alkylene chain completing a, 4, 5, or 6 membered ring structure.

Most preferred for use in the practice of the invention are poly-phosphorodiamide compounds in which:

X is oxygen;

$R_1, R_2, R_3, R_4, R_5, R_6, R_7$ and $R_8$ are hydrogen;

$R_9$ is alkylene having from 1 to about 6 carbon atoms, or phenylene; and $Z_1$ and $Z_2$ are the same or different and are

Wherein: $R_{10}$ is hydrogen, phenyl, alkyl having from 1 to 4 carbon atoms or cyclohexyl Especially effacious compounds for use in the practice of this invention are N,N'-bis-(diaminophosphinyl)-1,6-diaminohexane, N,N'-bis-(diaminophosphinyl)-1,8-diamino-p-menthane, N,N'-bis-(diaminophosphinyl)-piperazine, phosphorodiamidic acid 1,4-phenylene ester, phosphorodiamidic acid 1,3-phenylene ester, and phosphorodiamidic acid (1-methylethylidene)-di-4,1-phenylene ester.

Compounds for use in the practice of this invention can be prepared in accordance with the following reaction scheme:

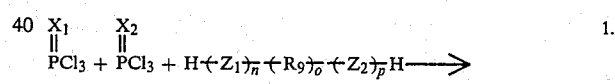

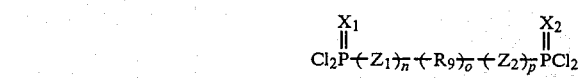

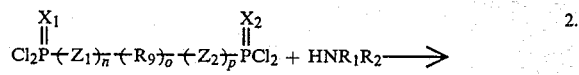

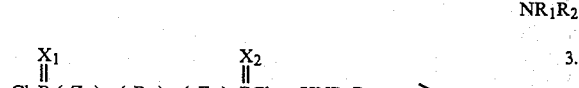

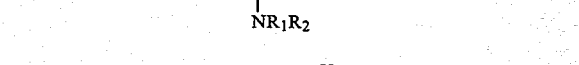

-continued

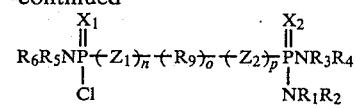

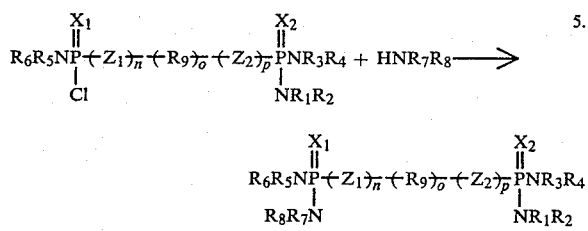

Wherein $X_1$, $X_2$, $Z_1$, $Z_2$, $R_1$, $R_2$, $R_3$, $R_4$, $R_5$, $R_6$, $R_7$, $R_8$ and $R_9$ are as described above. The aforementioned reaction is described in more detail in M. Goehring, K. Niedenzu, *Chem. Ber.* 89, p 1768; 1771 (1956), and V. V. Katyshkina and M. Ya. Kraft, *J. Gen. Chem., USSR*, 26, pp 3407–12 (1956) and references cited therein and will not be described herein in great detail.

Briefly stated in each step of the three step reaction sequence, substantially equal molar amounts or excesses of the reactants are contacted neat or in an inert solvent with or without a hydrogen chloride acid acceptor. Useful inert reaction solvents include ethyl ether, glyme, carbon tetrachloride, methylene chloride, benzene, dioxane, toluene, xylene, tetrahydrofuran, methyl sulfoxide, dimethylformamide, and the like.

The hydrogen chloride acid acceptor employed is a basic material which can be either an inorganic or organic base. Suitable inorganic bases include alkali metal carbonates such as sodium carbonate, potassium carbonate and the like. Organic bases which are useful and preferred for use in this invention are tertiary amines, as for example pyridine, lutidine, 1,4-diazabicyclo[2.2.2]octane, isoquinoline, quinoline, N-methylpiperidine, trimethylamine, triethylamine, and the like.

Reaction temperatures and pressures are not critical. The reaction can be conveniently carried out at a temperature of from about −30° C. to about 200° C., but is preferably carried out at a temperature of from about 0° C. to about 125° C. The reaction can be carried out at sub-atmospheric, atmospheric or super-atmospheric pressure. However, for convenience the reaction is usually carried out at atmospheric or autogeneous pressure.

The order in which the reactants are reacted indicated in the reaction scheme is for illustrative purposes only, and the order of reaction is not critical.

The exact proportions of the reactants are not critical, some of the desired product being obtained when the reactants are employed in any proportions. However, in going to completion, the reaction consumes the reactants and the hydrogen chloride acceptor in substantially equimolar proportions, and the use of the reactants and the hydrogen chloride acceptor in such proportion, is preferred, although an excess of the acceptor can be used.

Reaction times are not critical and can be varied widely depending on such factors as the reaction temperature, reactivity of the reactants and the like. The mixture is held within the desired reaction temperature range for a period of time, conveniently from about 2 to 8 hours before cooling. Good yields are obtained with reaction times of about 4 to 5 hours.

During the reaction, the hydrochloride salt of the hydrogen chloride acceptor forms and may precipitate from the mixture. This salt can be removed by such conventional procedures as extraction, filtration or centrifugation. The polyphosphorodiamide product can be separated by such conventional procedures as evaporation and purified by conventional procedures such as distillation and extraction. The product separated as described above may be employed in the control of urease in the soil in accordance with this invention or may be further purified by conventional procedures such as extraction and distillation.

The following specific examples are presented to more particularly illustrate the invention.

EXAMPLE I

Preparation of N,N'-Bis-(diaminophosphinyl)-1,6-diaminohexane

Hexamethylenediamine dihydrochloride (1.0 g, 5.3 mmol) was added to phosphorus oxychloride (6.0 mL, 9.9 g, 65 mmol). The mixture was stirred and refluxed for 6 hours. The excess of phosphorus oxychloride was distilled off (24° C., p=32−20 torr). The residue was dissolved in ether (50 mL), and was reacted with ammonia in ether (100 mL) at 0° C. to provide 2.0 g of a white solid, which consisted of the product (56%) and ammonium chloride (44%).

EXAMPLE II

Preparation of Phosphorodiamidic Acid 1,4-Phenylene Ester

A. A stirred mixture of 33.0 g (0.30 mol) of hydroquinone, 165 mL (276 g, 1.80 mol) of phosphorus oxychloride, and 0.99 g of potassium chloride was heated in a flask equipped with a condenser attached to a sodium hydroxide trap separated by a drying tube. The reaction solution became homogeneous at about 90° C., and evolution of hydrogen chloride gas commenced shortly thereafter. The temperature was raised until gentle reflux was attained (about 115° C.), while stirring was continued for 18 h. The temperature was lowered somewhat and the excess phosphorus oxychloride was removed by vacuum distillation. The remaining white cystals had a mp of 108°–118° C. and an $^1$H NMR (CDCl$_3$) showing mostly one singlet at δ7.40 ppm. The product could be freed from residual phosphorous oxychloride by washing with hexane, and, after drying, had a mp of 119°–123° C. The solid was dissolved in 150 mL of warm carbon tetrachloride, filtered to remove inorganic salts, and used directly in the next step.

B. The warm carbon tetrachloride solution from above was added dropwise to 750 mL of cold (0° C.) ether continuously saturated with ammonia gas. The addition required 1.5 h after which the ice-bath was removed and stirring was continued for another 45 minutes. The mixture was then filtered and washed with ether to give a white solid containing both the product and ammonium chloride. An $^1$H NMR (DMSO-d$_6$) showed a multiplet at δ7.10 for the aromatic protons and a broad singlet at δ4.35 ppm for the amidate protons. The product could be freed from most of the ammonium chloride by washing with a small amount of ice-water. The crude product containing ammonium chloride without further purification was satisfactory for use as a urease inhibitor.

EXAMPLE III

Preparation of N,N'-Bis-(diaminophosphinyl)-1,8-diamino-p-menthane 1,8-Diamino-p-menthane (32 g, 0.188 mol) was dissolved in anhydrous ether (500 mL), the solution was cooled to 0° C. and saturated with anhydrous hydrogen chloride. The precipitate of 1,8-diamino-p-menthane dihydrochloride was collected by filtration, rinsed with ether, and dried in vacuum at room temperature. The weight of the product was 12.5 g.

The dihydrochloride (3.2 g, 15 mmol) was refluxed with phosphorus oxychloride (20 mL, 215 mmol) for five hours. The excess of phosphorus oxychloride was distilled off at room temperature (p=28−12 torr). The residue was suspended in anhydrous ether and the slurry was saturated with ammonia. The product was dried in vacuum over $P_2O_5$.

EXAMPLE IV

Preparation of N,N'-Bis-(diaminophosphinyl)piperazine

Piperazine (1.72 g, 20 mmol) and pyridine (3.23 mL, 3.16 g, 40 mmol) were dissolved in anhydrous ether (110 mL). This solution was added over a 30 minute period to a solution of phosphorus oxychloride (3.66 mL, 6.13 g, 40 mmol) in 100 mL of ether with stirring under nitrogen at 0° C. The stirring was continued while allowing the reaction mixture to warm up to the ambient temperature (2 hours). The pyridine hydrochloride was removed by filtration, rinsed with ether, and the filtrate was added to a cold (0° C.) solution of ether (200 mL) saturated with anhydrous ammonia. The reaction mixture was stirred for 75 minutes at 0° C. The white solid (5.2 g) obtained was a mixture of the product with ammonium chloride, and was used as such for soil tests.

EXAMPLE V

Preparation of Phosphorodiamidic Acid (1-Methylethylidene)-di-4,1-Phenylene Ester A. A stirred mixture of 45.7 g (0.20 mol) of 4,4'-isopropylidenediphenol (bis-phenol-A), 110 mL (184 g, 1.2 mol) of phosphorus oxychloride, and 0.66 g of potassium chloride was heated in a flask equipped with a condenser attached to a sodium hydroxide trap separated by a drying tube. Heating was continued at reflux (about 110°–115° C.) for 12 h, and then excess phosphorus oxychloride was removed by vacuum distillation to give the intermediate dichloridate product as a clear oil. $^1$H NMR (CDCl$_3$): δ7.28 (s, 4, ArH) and 1.67 ppm (s, 3, CH$_3$).

B. The crude product from part A was dissolved in about 500 mL of ether, filtered free of inorganic salts, and added dropwise to 1000 mL of cold (0° C.) ether continuously saturated with ammonia gas. The addition was complete in 1.5 h, and copious amounts of a white solid had formed in the reaction flask. Stirring and the ammonia addition were continued for another 30 min. during which time the ice bath was removed. The solids were then collected by filtration, washed with ether and then with 2×300 mL of ice water, and dried in vacuo over $P_2O_5$ at 70° C. to give 75 g (97%) of crude product containing small amounts of ammonium chloride: mp—softens 138.5° C., dec. 192° C., $^1$H NMR (DMSO-d$_6$): δ7.2–6.8 (m, 4, ArH), 4.28 (br, d, 2, NH$_2$), and 1.60 ppm (s, 3, CH$_3$); $^{31}$P NMR (DMSO-d$_6$): δ14.9 ppm (s).

EXAMPLE VI

Preparation of Phosphorodiamidic Acid 1,3-Phenylene Ester

A. A stirred mixture of 33.0 g (0.30 mol) of resorcinol, 110 mL (184 g, 1.2 mol) of phosphorus oxychloride, and 0.66 g of potassium chloride was heated in a flask equipped with a condenser attached to a sodium hydroxide trap separated by a drying tube. Evolution of hydrogen chloride began at 110° C. Heating was continued at reflux (about 110° C.) for 18 h, and then excess phosphorus oxychloride was removed by vacuum distillation to give the intermediate dichloridate as an oil, $^1$H NMR (CDCl$_3$): δ7.38 (m, 2, ArH), 6.93 (m, 1, ArH), and about 7.7–6.3 (m, 1, ArH).

B. The oily chloride from part A was dissolved in 200 mL of ether, filtered free of inorganic salts, and added dropwise to 1300 mL of cold (0° C.) ether continuously saturated with ammonia gas. The addition was complete in 1.5 h, and then stirring and ammonia addition was continued for another 1 h during which time the ice bath was removed. A very sticky residue had formed in the reaction flask. The ether was decanted and a mixture of 500 mL of 95% ethanol and 150 mL of acetone was added. The mixture was then stirred vigorously for 1 h at room temperature and the mixture was filtered to remove ammonium chloride (31.4 g). Partial evaporation of the filtrate separated out more ammonium chloride (7 g), which was removed by filtration. Complete evaporation of the solvents left the product (38 g) as a slightly yellow oil that eventually solidified into a glassy material mp about 62° C.; $^1$H NMR (DMSO-d$_6$: δ7.5–6.9 (m, 3, ArH), 6.9–6.5 (m, 1, ArH), and 4.4 ppm (br s, 8, NH$_2$).

EXAMPLE VII

Efficacy Test

Efficacy tests were conducted to evaluate the efficacy of certain representative poly-phosphorodiamide compounds as urease inhibitors. The inhibition tests were run in a New York soil (Cazenovia silt loam, pH 7.2). Evaluations (run in triplicate) consisted of applying 800 micrograms of the test compound in 5 mL of water and 42.8 mg of urea in 1 mL of water to 20 g of air-dry soil in a glass bottle. The bottle was capped with perforated aluminum foil and incubated at 25° C. for three days prior to extraction with 100 mL of a 2M KCl solution containing 0.5 mg of phenylmercuric acetate. The extracts were then analyzed for remaining urea using an autoanalyzer. Percent inhibition was calculated as $$\% \text{ Inhibition} = \left(1 - \frac{A-B}{A-C}\right) \times 100\%$$

where A is urea recovered from unincubated sample (urea added to soil and immediately extracted); B is urea recovered from inhibited sample; and C is urea recovered from the control (uninhibited sample).

The results of these tests are set forth in the following Table I.

TABLE I

| Compound | % Inhibition |
| --- | --- |
| N,N'—Bis-(diaminophosphinyl)-1,6-diaminohexane | 86 |

TABLE I-continued

| Compound | % Inhibition |
| --- | --- |
| N,N'—Bis-(diaminophosphinyl)-1,8-diamino-p-menthane | 84 |
| N,N'Bis-diaminophosphinyl-piperazine | 76 |
| Phosphorodiamidic acid 1,4 phenylene ester | 90 |
| Phosphorodiamidic acid 1,3-phenylene ester | 81 |
| Phosphorodiamidic acid (1-methyl ethylidene)di-4,1-phenylene ester | 70 |

What is claimed is:

1. A composition comprising an acceptable carrier a urease inhibiting effective amount of one or more poly-phosphorodiamide compounds of the formula:

$$R_1R_2N-\overset{X_1}{\underset{R_3R_4N}{\overset{\|}{P}}}(Z_{1n})(R_{9o})(Z_{2p})\overset{X_2}{\underset{NR_7R_8}{\overset{\|}{P}}}-NR_5R_6$$

Wherein:
  n, o and p are the same or different and are 0 or 1, with the proviso that at least one of n, o and p is 1;
  $X_1$ and $X_2$ are the same or different and are oxygen or sulfur;
  $R_1$, $R_2$, $R_3$, $R_4$, $R_5$, $R_6$, $R_7$ and $R_8$ are the same or different and are hydrogen or alkyl having from 1 to about 4 carbon atoms;
  $R_9$ is substituted or unsubstituted divalent aminophosphinyl, alkynylene, alkylene, alkenylene, cycloalkylene, cycloalkenylene, or arylene groups which groups may include one or more divalent oxygen, nitrogen, sulfur, sulfonyl, sulfinyl, or carbamyl functions, wherein permissible substituents include one or more amino, alkylamino, dialkylamino, arylamino, mercapto, alkylmercapto, S-diaminophosphinyl, N-diaminophosphinyl, O-diaminophosphinyl, N-(diaminophosphinyl)carbamyl, halogen, hydroxy, sulfonic acid, alkyl, alkoxy, nitro or cyano groups;
  $Z_1$ and $Z_2$ are the same or different and are divalent oxygen, sulfur, or a divalent carbamyl or amino moiety of the formula:

$$-\overset{O}{\overset{\|}{C}}-\overset{R_{10}}{\underset{}{\overset{|}{N}}}- \quad \text{or} \quad -\overset{R_{10}}{\underset{}{\overset{|}{N}}}-$$

Wherein: $R_{10}$ is hydrogen or substituted or unsubstituted cycloalkyl, alkyl, diaminophosphinyl, or phenyl wherein permissible substituents include one or more halogen, nitro, cyano, trifluoromethyl, alkoxy, N-diaminophosphinyl, O-diaminophosphinyl, S-diaminophosphinyl, N-(diaminophosphinyl)carbamyl, alkylmercapto, and mercapto groups or any two $R_{10}$ substituents together may form an alkylene chain completing a 4, 5, 6, 7, or 8 membered ring structure.

2. A composition according to claim 1 wherein said urease inhibiting amount is at least about 0.00001 weight percent based on the total weight of the composition.

3. A composition according to claim 2 wherein said amount is from about 0.00001 to about 98 weight percent.

4. A composition according to claim 3 wherein said amount is from about 0.001 to about 50 weight percent.

5. A composition according to claim 4 wherein said amount is from about 0.002 to about 20 weight percent.

6. A composition according to claim 1 wherein $X_1$ and $X_2$ are oxygen.

7. A composition according to claim 1 wherein $R_1$ $R_2$, $R_3$, $R_4$, $R_5$, $R_6$, $R_7$, $R_8$ are hydrogen.

8. A composition according to claim 1 wherein $R_9$ is divalent aminophosphinyl, alkylene, phenylene, alkylenephenylalkylene, alkyleneaminoalkylene, or oxoalkyleneoxo, either unsubstituted or substituted with one or more halogen, alkyl, nitro, cyano, S-diaminophosphinyl, N-diaminophosphinyl, O-diaminophosphinyl, N-(diaminophosphinyl)carbamyl, trihalomethyl or alkoxy substituents.

9. A composition according to claim 8 wherein $R_9$ is phenylene, alkylene having from 1 to about 6 carbon atoms, alkyleneaminoalkylene having from about 2 to about 8 carbon atoms or alkylphenylene having from about 7 to about 14 carbon atoms.

10. A composition according to claim 9 wherein $R_9$ is alkylene having from 1 to about 6 carbon atoms or phenylene.

11. A composition according to claim 1 wherein $Z_1$ and $Z_2$ are the same or different and are divalent oxygen or a moiety of the formula:

$$-\overset{R_{10}}{\underset{}{\overset{|}{N}}}-$$

Wherein: $R_{10}$ is hydrogen, alkyl, cycloalkyl, O-diaminophosphinyl, N-diaminophosphinyl, phenyl, alkyl substituted with one or more halogen substituents, phenyl substituted with one or more alkyl, nitro, aryloxy, halogen or trihalomethyl, or two $R_{10}$ substituents together may form an alkylene chain completing a 4, 5, or 6 membered ring structure which may be substituted with one or more of the aforementioned substituents.

12. A composition according to claim 11 wherein $Z_1$ and $Z_2$ are the same or different and are divalent oxygen or a moiety of the formula:

$$-\overset{R_{10}}{\underset{}{\overset{|}{N}}}-$$

Wherein: $R_{10}$ is hydrogen, N-diaminophosphinyl, O-diaminophosphinyl, cyclohexyl or substituted or unsubstituted alkyl or phenyl wherein permissible substituents are one or more halogen groups or two $R_{10}$ groups together may form an alkylene chain completing a 4, 5 or 6 membered ring structure.

13. A composition according to claim 12 wherein $Z_1$ and $Z_2$ are the same or different and are a moiety of the formula:

$$-\overset{R_{10}}{\underset{}{\overset{|}{N}}}-$$

Wherein: $R_{10}$ is hydrogen, phenyl, cyclohexyl or alkyl having from 1 to about 4 carbon atoms.

14. A composition according to claim 13 wherein $Z_1$ and $Z_2$ are the same.

15. A composition according to claim 1 wherein said one or more poly-phosphorodiamide compounds are selected from the group consisting of N,N'-bis-(diaminophosphinyl)-1,6-diaminohexane, N,N'-bis-(diaminophosphinyl)-1,8-diamino-p-menthane, N,N'- bis-(diaminophosphinyl)-piperazine, phosphorodiamidic acid 1,4-phenylene ester, phosphorodiamidic acid 1,3-phenylene ester and phosphorodiamidic acid (1-methylethyledine)-di-4,1-phenylene ester.

16. A composition according to claim 15 wherein said one or more compounds are selected from the group consisting of N,N'-bis-(diaminophosphinyl)-1,6-diamino hexane, N,N'-bis-(diaminophosphinyl)-1,8-diamino-p-menthane and phosphorodiamidic acid 1,4-phenylene ester.

17. A composition according to claim 16 wherein said compound is phosphorodiamidic acid 1,4-phenylene ester.

18. A composition according to claim 10 wherein $R_9$ is phenylene.

19. A method of inhibiting the urease catalyzed hydrolysis of urea at a situs which comprises applying to said situs a urease inhibiting effective amount of one or more compounds of the formula:

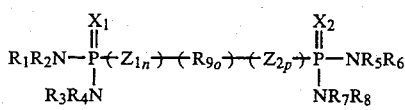

Wherein:
n, o and p are the same or different and are 0 or 1, with the proviso that at least one of n, o or p is 1;
$X_1$ and $X_2$ are the same or different and are oxygen or sulfur;
$R_1$, $R_2$, $R_3$, $R_4$, $R_5$, $R_6$, $R_7$ and $R_8$ are the same or different and are hydrogen or alkyl having from 1 to about 4 carbon atoms;
$R_9$ is substituted or unsubstituted divalent aminophosphinyl alkynylene, alkylene, alkenylene, cycloalkylene, cycloalkenylene, or arylene groups which groups may include one or more divalent oxygen, nitrogen, sulfur, sulfonyl, sulfinyl, or carbamyl functions, wherein permissible substituents include one or more amino, alkylamino, dialkylamino, arylamino, mercapto, alkylmercapto, S-diaminophosphinyl, N-diaminophosphinyl, O-diaminophosphinyl, N-(diaminophosphinyl)carbamyl, halogen, hydroxy, sulfonic acid, alkyl, alkoxy, nitro or cyano groups;
$Z_1$ and $Z_2$ are the same or different and are divalent oxygen, sulfur, or a divalent carbamyl or amino moiety of the formula:

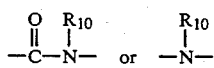

Wherein: $R_{10}$ is hydrogen or substituted or unsubstituted cycloalkyl, alkyl, diaminophosphinyl, or phenyl wherein permissible substituents include one or more halogen, nitro, cyano, trifluoromethyl, alkoxy, N-diaminophosphinyl, O-diaminophosphinyl, S-diaminophosphinyl, N-(diaminophosphinyl)carbamyl, alkylmercapto, and mercapto groups or any two $R_{10}$ substituents together may form an alkylene chain completing a 4, 5, 6, 7, or 8 membered ring structure.

20. A method according to claim 18 wherein said situs is a plant growth media.

21. A method according to claim 20 wherein urea and/or a compound capable of forming urea in situ are applied to said plant growth media prior to, subsequent to or in conjunction with the application of said compounds to said media.

22. A method according to claim 20 wherein said urease inhibiting effective amount is at least about 0.01 ppm.

23. A method according to claim 22 wherein said amount is from about 0.01 to about 5000 ppm.

24. A method according to claim 23 wherein said amount is from about 2 to about 1000 ppm.

25. A method according to claim 24 wherein said amount is from about 10 to about 500 ppm.

26. An improved fertilizer composition which comprises urea and/or one or more compounds capable of forming urea in situ under the use conditions of the composition and a urease inhibiting effective amount of one or more poly-phosphorodiamide compounds of the formula:

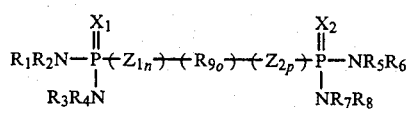

Wherein:
n, o and p was the same or different and are 0 or 1, with the proviso that at least one of n, o or p is 1;
$X_1$ and $X_2$ are the same or different and are oxygen or sulfur;
$R_1$, $R_2$, $R_3$, $R_4$, $R_5$, $R_6$, $R_7$ and $R_8$ are ths same or different and are hydrogen or alkyl having from 1 to about 4 carbon atoms;
$R_9$ is substituted or unsubstituted divalent aminophosphinyl, alkynylene, alkylene, alkenylene, cycloalkylene, cycloalkenylene, or arylene groups which groups may include one or more divalent oxygen, nitrogen, sulfur, sulfinyl, sulfonyl or carbamyl functions, wherein permissible substituents include one or more mercapto, alkylmercapto, S-diaminophosphinyl, N-diaminophosphinyl, O-diaminophosphinyl, N-(diaminophosphinyl)carbamyl, halogen, hydroxy, sulfonic acid, dialkylamino, arylamino, amino, alkylamino, alkyl, alkoxy, nitro or cyano groups;
$Z_1$ and $Z_2$ are the same or different and are divalent oxygen, sulfur, or a divalent carbamyl or amino moiety of the formula:

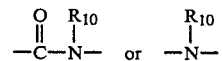

Wherein: $R_{10}$ is hydrogen or substituted or unsubstituted cycloalkyl, alkyl, diaminophosphinyl, or phenyl wherein permissible substituents include one or more halogen, nitro, cyano, trifluoromethyl, alkoxy, N-diaminophosphinyl, O-diaminophosphinyl, S-diaminophosphinyl, N-(diaminophosphinyl)carbamyl, alkylmercapto, and mercapto groups or any two $R_{10}$ substituents together may from an alkylene chain completing a 4, 5, 6, 7, or 8 membered ring structure.

27. A method of enhancing plant growth and crop yield which comprises applying an effective amount of the composition according to claim 26 to a plant growth media within the root zone of said plant.

28. A compound of the formula:

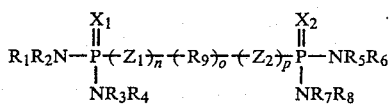

Wherein:
- n, o and p are the same or different and are 0 are 1, with the proviso that at least one of n, o and p is 1;
- $X_1$ and $X_2$ are the same or different and are oxygen of sulfur;
- $R_1$, $R_2$, $R_3$, $R_4$, $R_5$, $R_6$, $R_7$ and $R_8$ are the same or different and are hydrogen or alkyl having from 1 to about 4 carbon atoms;
- $R_9$ is a substituted or unsubstituted divalent aminophosphinyl, alkynylene, alkylene, alkenylene, cycloalkylene, cycloalkenylene, or arylene groups which groups may include one or more divalent oxygen, nitrogen, sulfur, sulfonyl, sulfinyl, or carbamyl functions, wherein permissible substituents include one or more amino, alkylamino, dialkylamino, arylamino, mercapto, alkylmercapto, S-diaminophosphinyl, N-diaminophosphinyl, O-diaminophosphinyl, N-(diaminophosphinyl)carbamyl, halogen, hydroxy, sulfonic acid, alkyl, alkoxy, nitro or cyano groups;
- $Z_1$ and $Z_2$ are the same or different and are divalent oxygen, sulfur, or a divalent carbamyl or amino moiety of the formula:

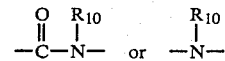

Wherein: $R_{10}$ is hydrogen or substituted or unsubstituted cycloalkyl, alkyl, diaminophosphinyl, or phenyl wherein permissible substituents include one or more halogen, nitro, cyano, trifluoromethyl, alkoxy, N-diaminophosphinyl, O-diaminophosphinyl, S-diaminophosphinyl, N-(diaminophosphinyl)carbamyl, alkylmercapto, and mercapto groups or any two $R_{10}$ substituents together may form an alkylene chain completing a 4, 5, 6, 7, or 8 membered ring structure.

29. A compound according to claim 28 wherein $R_1$, $R_2$, $R_3$, $R_4$, $R_5$, $R_6$, $R_7$, and $R_8$ are hydrogen.

30. A composition according to claim 1 wherein said carrier is a liquid.

31. A composition according to claim 30 wherein said liquid carrier is selected from the group consisting of water and organic liquids.

32. A composition according to claim 1 wherein said carrier is a finely divided inert solid.

* * * * *

UNITED STATES PATENT AND TRADEMARK OFFICE
CERTIFICATE OF CORRECTION

PATENT NO. : 4,518,413
DATED : May 21, 1985
INVENTOR(S) : Michael D. Swerdloff et al.

It is certified that error appears in the above-identified patent and that said Letters Patent are hereby corrected as shown below:

Col. 20, line 10, "witn" should read -- with --.

Signed and Sealed this

Third Day of December 1985

[SEAL]

Attest:

DONALD J. QUIGG

Attesting Officer  Commissioner of Patents and Trademarks